US00PP30689P2

(12) United States Plant Patent
Koot et al.

(10) Patent No.: US PP30,689 P2
(45) Date of Patent: Jul. 9, 2019

(54) **NEW GUINEA *IMPATIENS* PLANT NAMED 'DOIMTATRURE'**

(50) Latin Name: *Impatiens hawkeri*
Varietal Denomination: Doimtatrure

(71) Applicant: DUMMEN GROUP B.V., De Lier (NL)

(72) Inventors: Arjan Koot, Oeffelt (NL); Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,832

(22) Filed: May 1, 2018

(51) Int. Cl.
*A01H 5/02* (2018.01)

(52) U.S. Cl.
USPC ..... Plt./318.7
CPC ..... *A01H 5/02* (2013.01)

(58) Field of Classification Search
USPC ..... Plt./318.7
CPC ..... A01H 5/0261
See application file for complete search history.

*Primary Examiner* — Kent L Bell
(74) *Attorney, Agent, or Firm* — C. A. Whealy

(57) ABSTRACT

A new and distinct cultivar of *Impatiens* plant named 'Doimtatrure' characterized by its upright, outwardly spreading and mounding plant habit; moderately vigorous growth habit; freely branching habit; dark green-colored leaves; freely and early flowering habit; relatively large bright red-colored flowers; and good garden performance.

1 Drawing Sheet

Botanical designation: *Impatiens hawkeri.*
Cultivar denomination: 'DOIMTATRURE'.

BACKGROUND OF THE INVENTION

The present invention relates to a new and distinct cultivar of New Guinea *Impatiens* plant, botanically known as *Impatiens hawkeri* and hereinafter referred to by the name 'Doimtatrure'.

The new *Impatiens* plant is a product of a planned breeding program conducted by the Inventors in Koka, Ethiopia and Rheinberg, Germany. The objective of the breeding program is to create new early and freely flowering New Guinea *Impatiens* plants with large attractive flowers and good garden performance.

The new *Impatiens* plant originated from a cross-pollination made by the Inventors in November, 2012 in Koka, Ethiopia of a proprietary selection of *Impatiens hawkeri* identified as code number NN-1161, not patented, as the female, or seed, parent with a proprietary selection of *Impatiens hawkeri* identified as code number NN10-003550-005, not patented, as the male, or pollen, parent. The new *Impatiens* plant was discovered and selected by the Inventors as a single flowering plant from within the progeny of the stated cross-pollination in a controlled greenhouse environment in Rheinberg, Germany in April, 2013.

Asexual reproduction of the new *Impatiens* plant by terminal vegetative cuttings in a controlled greenhouse environment in Rheinberg, Germany since June, 2013 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Doimtatrure'. These characteristics in combination distinguish 'Doimtatrure' as a new and distinct *Impatiens* plant:

1. Upright, outwardly spreading and mounding plant habit.
2. Moderately vigorous growth habit.
3. Freely branching habit.
4. Dark green-colored leaves.
5. Freely and early flowering habit.
6. Relatively large bright red-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* flower earlier than plants of the female parent selection.
2. Plants of the new *Impatiens* have larger flowers than plants of the female parent selection.

Plants of the new *Impatiens* can be compared to plants of the male parent selection. Plants of the new *Impatiens* differ primarily from plants of the male parent selection in the following characteristics:

1. Plants of the new *Impatiens* are not as broadly spreading as plants of the male parent selection.
2. Plants of the new *Impatiens* have larger flowers than plants of the male parent selection.

Plants of the new *Impatiens* can be compared to plants of *Impatiens hawkeri* 'Tamar Dark Red', disclosed in U.S. Plant Pat. No. 19,423. In side-by-side comparisons, plants of the new *Impatiens* differ primarily from plants of 'Tamar Dark Red' in the following characteristics:

1. Plants of the new *Impatiens* flower earlier than plants of 'Tamar Dark Red'.
2. Plants of the new *Impatiens* have larger flowers than plants of 'Tamar Dark Red'.

Plants of the new *Impatiens* can also be compared to plants of *Impatiens hawkeri* 'Duemagwis', disclosed in U.S. Plant Pat. No. 26,782. In side-by-side comparisons, plants of the new *Impatiens* differ primarily from plants of 'Duemagwis' in the following characteristics:

1. Leaves of plants of the new *Impatiens* and 'Duemagwis' differ in lower surface color as lower surfaces of leaves of plants of 'Duemagwis' are red purple in color.
2. Plants of the new *Impatiens* flower earlier than plants of 'Duemagwis'.
3. Plants of the new *Impatiens* and 'Duemagwis' differ in flower color as plants of 'Duemagwis' have light red-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet comprises a side perspective view of a typical flowering plant of 'Doimtatrure' grown in a container.

The photograph at the top of the sheet is a close-up view of a typical flowering plant of 'Doimtatrure'.

DETAILED BOTANICAL DESCRIPTION

The aforementioned photographs and following observations, measurements and values describe plants grown during the winter in 16.5-cm containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 4,500 to 5,500 lux. Plants were 25 weeks old when the photographs and description were taken. In the following description, color references are made to The Royal Horticultural Society Colour Chart, 2007 Edition, except where general terms of ordinary dictionary significance are used.

Botanical classification: *Impatiens hawkeri* 'Doimtatrure'.

Parentage:

*Female, or seed, parent*.—Proprietary selection of *Impatiens hawkeri* identified as code number NN-1161, not patented.

*Male, or pollen, parent*.—Proprietary selection of *Impatiens hawkeri* identified as code number NN10-003550-005, not patented.

Propagation:

*Type*.—By terminal vegetative cuttings.

*Time to initiate roots, summer and winter*.—About five to seven days at temperatures about 20° C.

*Time to produce a rooted young plant, summer and winter*.—About three to four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and mounding plant habit; freely branching habit with about eight primary lateral branches each with about two to four secondary lateral branches developing per plant; moderately vigorous growth habit and moderate to rapid growth rate.

*Height, soil level to top of foliar plane*.—About 22 cm.

*Height, soil level to top of floral plane*.—About 23.5 cm.

*Plant diameter or spread*.—About 45 cm.

Lateral branch description:

*Length*.—About 21 cm.

*Diameter, primary lateral branches*.—About 1.2 cm.

*Diameter, secondary lateral branches*.—About 9 mm.

*Internode length*.—About 5.2 cm.

*Strength*.—Strong.

*Aspect*.—About 45° from vertical.

*Texture and luster*.—Smooth, glabrous; semi-glossy.

*Color, when developing*.—Close to 187A.

*Color, fully developed*.—Close to 187A.

Leaf description:

*Arrangement*.—Opposite or in whorls of four to six leaves; simple.

*Length*.—About 11.8 cm.

*Width*.—About 4.6 cm.

*Shape*.—Elliptical.

*Apex*.—Acuminate.

*Base*.—Attenuate.

*Margin*.—Entire with ciliation.

*Texture and luster, upper surface*.—Smooth, glabrous; slightly glossy.

*Texture and luster, lower surface*.—Smooth, glabrous; matte.

*Venation pattern*.—Pinnate; arcuate.

*Color*.—Developing leaves, upper surface: Close to 147A. Developing leaves, lower surface: Close to 147B. Fully expanded leaves, upper surface: Darker than 147A; venation, close to 148C. Fully expanded leaves, lower surface: Close to 147B; venation, close to 187B.

*Petioles*.—Length: About 4.2 cm. Diameter: About 3 mm. Strength: Strong. Texture, upper and lower surfaces: Smooth, glabrous; slightly glossy. Color, upper surface: Close to 185A. Color, lower surface: Close to 187C.

Flower description:

*Flower type and flowering habit*.—Relatively large single rounded to axillary flowers; freely flowering habit, typically about 152 flowers developing per plant; flowers positioned above and beyond the foliar plane; flowers typically face mostly upright to outwardly.

*Flower longevity*.—Flowers typically last about two to three days on the plant under greenhouse conditions; petals self-cleaning, gynoecium persistent.

*Fragrance*.—None detected.

*Natural flowering season*.—Year-round under greenhouse conditions; in the garden, flowering continuous from spring until fall in California; early flowering habit, plants typically begin flowering about twelve weeks after planting.

*Flower buds*.—Length: About 3 cm. Diameter: About 1.8 cm. Shape: Ovate. Texture and luster: Smooth, glabrous; slightly glossy. Color: Close to 46B.

*Flower diameter*.—About 7 cm.

*Flower depth*.—About 2 cm; with spur, about 6.5 cm.

*Petals*.—Quantity and arrangement: Five per flower in a single whorl. Banner petals, length: About 3.2 cm. Banner petals, width: About 5.6 cm. Lateral petals, length: About 3 cm. Lateral petals, width: About 4.6 cm. Lower petals, length: About 4 cm. Lower petals, width: About 4.5 cm. Shape: Cordate. Apex: Emarginate. Base: Attenuate. Margin: Entire; margins on lateral petals are slightly upright. Texture and luster, upper and lower surfaces: Smooth, glabrous; velvety; matte. Color: When opening, upper surface: Close to 46A. When opening, lower surface: Close to 46B. Fully opened, upper surface: Close to 46B; towards the base, tinged with close to N78C; venation, close to 46B; color does not fade with development. Fully opened, lower surface: Close to 46C; venation, close to 46C; color does not fade with development.

*Sepals*.—Quantity and arrangement: Three in a single whorl; two lateral sepals and one center sepal modified into an elongated spur. Lateral sepals, length: About 1.5 cm. Lateral sepals, width: About 7 mm. Center sepals, length: About 2 cm. Center sepals, width: About 1.5 cm. Shape: Elliptical. Apex: Acuminate. Base, lateral sepals: Truncate. Base, center sepal: Modified into a straight spur, fused into a slender tube. Margin: Entire. Texture and luster, upper and lower surfaces: Smooth, glabrous; slightly glossy. Color: When opening, upper surface: Close to 185C. When opening, lower surface: Close to 183C to 183D. Fully opened, upper surface: Close to 185C; towards the apex of the center sepal, close to 185B. Fully opened, lower surface: Close to 185C. Spur length: About 5.6 cm. Spur diameter: At the flower, about 2 mm. Spur texture and luster: Smooth, glabrous; moderately glossy. Spur color: Close to 187B.

*Peduncles*.—Length: About 4.6 cm. Diameter: About 2 mm. Angle: About 45° from branch axis. Strength: Strong. Texture and luster: Smooth, glabrous; moderately glossy. Color: Close to 187B.

*Reproductive organs*.—Stamens: Quantity: Five fused at anthers; filaments free. Filament length: About 3 mm. Filament color: Close to 46B. Anther size: About 3 mm by 5 mm. Anther shape: Oblong. Anther color: Close to 46B. Pollen amount: Moderate. Pollen color: Close to 158B. Pistils: Quantity per flower: One. Pistil length: About 8 mm. Stigma diameter: About 2 mm. Stigma shape: Rounded. Stigma color: Close to 145C. Style length: About 1 mm. Style color: Close to 145C. Ovary color: Close to 46A tinted with close to 183A.

*Seeds and fruits*.—To date, seed and fruit production has not been observed on plants of the new *Impatiens* to date.

Pathogen & pest resistance: To date, plants of the new *Impatiens* have not been observed to be resistant to pathogens and pests common to *Impatiens* plants to date.

Garden performance: Plants of the new *Impatiens* have been observed to have good garden performance and tolerate temperatures ranging from about 5° C. to about 40° C.

It is claimed:

1. A new and distinct *Impatiens* plant named 'Doimtatrure' as illustrated and described.

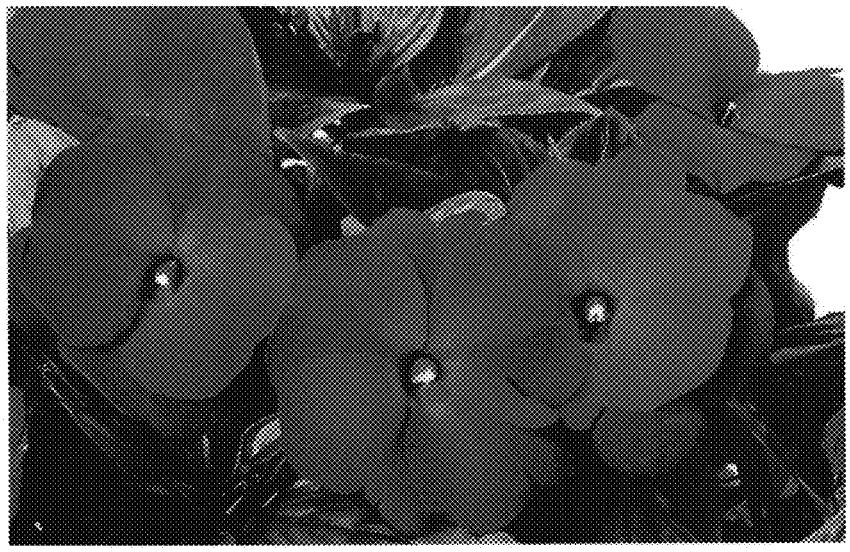
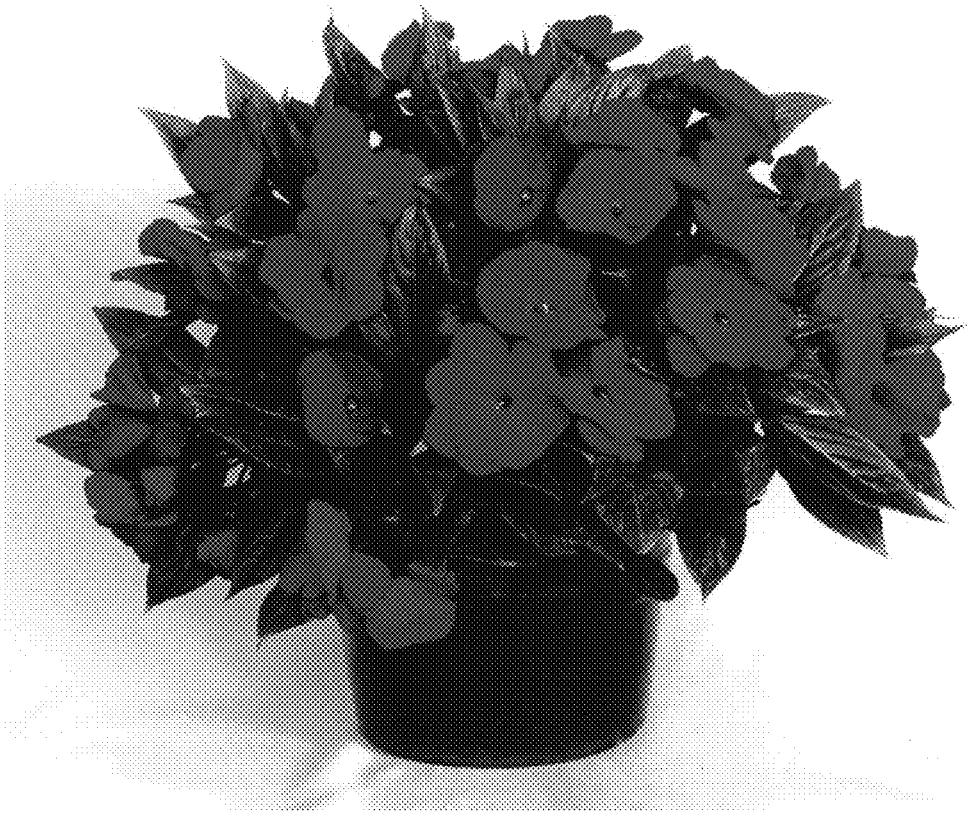

* * * * *